US011414605B2

(12) United States Patent
Ouni et al.

(10) Patent No.: US 11,414,605 B2
(45) Date of Patent: Aug. 16, 2022

(54) USE OF RENEWABLE OIL IN HYDROTREATMENT PROCESS

(71) Applicant: Neste Oyj, Espoo (FI)

(72) Inventors: Tuomas Ouni, Helsinki (FI); Väinö Sippola, Espoo (FI); Petri Lindqvist, Porvoo (FI)

(73) Assignee: NESTE OYJ, Espoo (FI)

( * ) Notice: Subject to any disclaimer, the term of this patent is extended or adjusted under 35 U.S.C. 154(b) by 4 days.

(21) Appl. No.: 17/184,984

(22) Filed: Feb. 25, 2021

(65) Prior Publication Data

US 2021/0179947 A1 Jun. 17, 2021

Related U.S. Application Data

(63) Continuation of application No. 16/458,979, filed on Jul. 1, 2019, now Pat. No. 10,954,451, which is a continuation of application No. 15/954,501, filed on Apr. 16, 2018, now Pat. No. 10,385,278, which is a continuation of application No. 14/932,566, filed on Nov. 4, 2015, now Pat. No. 9,969,940, which is a continuation of application No. 14/273,024, filed on May 8, 2014, now Pat. No. 9,206,092, which is a continuation of application No. 13/397,236, filed on Feb. 15, 2012, now Pat. No. 8,742,185.

(60) Provisional application No. 61/443,161, filed on Feb. 15, 2011.

(30) Foreign Application Priority Data

Feb. 15, 2011 (EP) .................... 11154437

(51) Int. Cl.
| | | |
|---|---|---|
| *C10G 45/58* | (2006.01) | |
| *C10G 3/00* | (2006.01) | |
| *A23D 9/007* | (2006.01) | |
| *C11C 3/12* | (2006.01) | |
| *C07C 1/207* | (2006.01) | |
| *C07C 5/27* | (2006.01) | |
| *C07C 69/604* | (2006.01) | |
| *C07C 69/66* | (2006.01) | |

(52) U.S. Cl.
CPC .............. *C10G 3/50* (2013.01); *A23D 9/007* (2013.01); *C07C 1/207* (2013.01); *C07C 5/27* (2013.01); *C07C 69/604* (2013.01); *C07C 69/66* (2013.01); *C10G 3/46* (2013.01); *C10G 45/58* (2013.01); *C11C 3/126* (2013.01); *C10G 2300/1014* (2013.01); *C10G 2300/1018* (2013.01); *C10G 2300/205* (2013.01); *C10G 2400/02* (2013.01); *C10G 2400/04* (2013.01); *C10G 2400/08* (2013.01); *C10G 2400/10* (2013.01); *C10G 2400/18* (2013.01); *C10G 2400/28* (2013.01); *Y02P 30/20* (2015.11)

(58) Field of Classification Search
None
See application file for complete search history.

(56) References Cited

U.S. PATENT DOCUMENTS

| | | |
|---|---|---|
| 2,093,159 A | 9/1937 | Otto |
| 3,147,210 A | 9/1964 | Hass et al. |
| 3,496,099 A | 2/1970 | Bridge |
| 3,663,434 A | 5/1972 | Bridge |
| 3,767,562 A | 10/1973 | Sze et al. |
| 3,929,615 A | 12/1975 | Linden et al. |
| 4,300,009 A | 11/1981 | Haag et al. |
| 4,512,878 A | 4/1985 | Reid et al. |
| 4,518,485 A | 5/1985 | Lapierre et al. |
| 4,629,588 A | 12/1986 | Welsh et al. |
| 4,992,605 A | 2/1991 | Craig et al. |
| 5,079,208 A | 1/1992 | Lammers et al. |
| 5,093,535 A | 3/1992 | Harrison et al. |
| 5,298,639 A | 3/1994 | Toeneboehn et al. |
| 5,705,722 A | 1/1998 | Monnier et al. |
| 5,882,505 A | 3/1999 | Wittenbrink et al. |
| 5,888,376 A | 3/1999 | Wittenbrink et al. |
| 5,906,729 A | 5/1999 | Chou |
| 6,123,835 A | 9/2000 | Ackerson et al. |
| 6,203,695 B1 | 3/2001 | Harle et al. |
| 6,656,342 B2 | 12/2003 | Smith et al. |
| 8,212,094 B2 | 7/2012 | Myllyoja et al. |
| 8,278,492 B2 | 10/2012 | Myllyoja et al. |
| 8,658,020 B2 | 2/2014 | Alvarez et al. |

(Continued)

FOREIGN PATENT DOCUMENTS

| | | |
|---|---|---|
| CZ | 283575 B6 | 5/1998 |
| EP | 0507217 A1 | 10/1992 |

(Continued)

OTHER PUBLICATIONS

Printout of http://blog.minitab.com/blog/adventures-in-statistics-2/regression-analysis-how-do-i-interpret-r-squared-and-assess-the-goodness-of-fit, May 30, 2013.
Declaration of Pekka Aalto under 37 CF.R. § 1.132, dated Nov. 14, 2012, in Reexamination Control No. 95/002,084.
*Align Technology, Inc.* v. *ClearCorrect Operating, LLC*, Appeal No. 2017-2106, 2018 BL 310554 (Fed. Cir. Aug. 22, 2018), Exhibit 2001 in Inter Partes Review No. IPR2018-01374.
Amended Petition dated Dec. 13, 2013 in Inter Partes Review No. IPR2014-00192.

(Continued)

*Primary Examiner* — Tam M Nguyen
(74) *Attorney, Agent, or Firm* — Buchanan Ingersoll & Rooney PC

(57) ABSTRACT

The use of bio oil from at least one renewable source in a hydrotreatment process, in which process hydrocarbons are formed from said glyceride oil in a catalytic reaction, and the iron content of said bio oil is less than 1 w-ppm calculated as elemental iron. A bio oil intermediate including bio oil from at least one renewable source and the iron content of said bio oil is less than 1 w-ppm calculated as elemental iron.

7 Claims, 3 Drawing Sheets

(56) References Cited

U.S. PATENT DOCUMENTS

| | | | |
|---|---|---|---|
| 8,961,794 B2 | 2/2015 | Fjare et al. | |
| 9,328,303 B2 | 5/2016 | Abhari et al. | |
| 9,371,256 B2 | 6/2016 | Yao et al. | |
| 9,523,041 B2 | 12/2016 | Abhari et al. | |
| 2001/0027937 A1 | 10/2001 | Tsao et al. | |
| 2003/0050492 A1 | 3/2003 | Copeland et al. | |
| 2006/0293532 A1 | 12/2006 | Lee et al. | |
| 2007/0010682 A1 | 1/2007 | Myllyoja et al. | |
| 2008/0154073 A1 | 6/2008 | Petri et al. | |
| 2009/0266743 A1 | 10/2009 | Yao et al. | |
| 2009/0300970 A1* | 12/2009 | Perego | C10G 45/60 44/307 |
| 2009/0300972 A1* | 12/2009 | Jalalpoor | C10L 1/026 422/261 |
| 2010/0000908 A1 | 1/2010 | Markkanen et al. | |
| 2010/0038284 A1 | 2/2010 | Vergel | |
| 2010/0056833 A1 | 3/2010 | Suarez et al. | |
| 2010/0132251 A1 | 6/2010 | Sohling et al. | |
| 2010/0240942 A1 | 9/2010 | Daudin et al. | |
| 2010/0325943 A1* | 12/2010 | Chapus | C10G 3/48 44/308 |
| 2011/0049012 A1 | 3/2011 | Stigsson et al. | |
| 2011/0077436 A1 | 3/2011 | Yao et al. | |
| 2011/0138680 A1 | 6/2011 | Dandeu et al. | |
| 2011/0144364 A1* | 6/2011 | Dandeu | C11C 3/003 554/167 |
| 2011/0239532 A1* | 10/2011 | Baldiraghi | C10G 67/02 44/388 |
| 2011/0258916 A1* | 10/2011 | Baldiraghi | C10G 3/47 44/388 |
| 2012/0137572 A1 | 6/2012 | Bartek et al. | |
| 2012/0209017 A1* | 8/2012 | Ouni | C11C 3/126 585/254 |
| 2012/0238787 A1 | 9/2012 | Gruber et al. | |
| 2013/0216688 A1* | 8/2013 | Bruinsma | B01D 11/0288 426/624 |
| 2014/0123662 A1* | 5/2014 | Ramirez Corredores | C10G 1/02 44/307 |
| 2014/0243541 A1 | 8/2014 | Ouni et al. | |
| 2016/0060540 A1 | 3/2016 | Ouni et al. | |
| 2017/0022424 A1 | 1/2017 | Chapus et al. | |
| 2018/0305622 A1 | 10/2018 | Ouni et al. | |
| 2018/0334618 A1* | 11/2018 | Freel | C10B 53/02 |
| 2019/0322947 A1 | 10/2019 | Ouni et al. | |

FOREIGN PATENT DOCUMENTS

| | | |
|---|---|---|
| EP | 1396531 A2 | 3/2004 |
| FI | 933982 A | 9/1993 |
| FI | 100248 B | 10/1997 |
| FR | 2151059 A1 | 4/1973 |
| FR | 2607803 A1 | 6/1988 |
| FR | 2937647 A1 | 4/2010 |
| GB | 1002922 A | 9/1965 |
| GB | 1524781 A | 9/1978 |
| SE | 520633 C2 | 8/2003 |
| WO | 9216601 A1 | 10/1992 |
| WO | 2007003709 A1 | 1/2007 |

OTHER PUBLICATIONS

Amended Petition dated Mar. 21, 2013 in Inter Partes Review No. IPR2013-00178.
Canola Laboratory Report, Summit Environmental Technologies, issued Feb. 27, 2013 (Ex. 1005 in IPR2013-00178).
European Committee for Standardization (CEN), EN 14241, Chimneys—Elastomeric seals and elastomeric sealants—Material requirements and test methods, 2013 (DIN, Berlin, Germany).
IUPAC, Compendium of Chemical Terminology: Gold Book, 2nd ed., Compiled by A. D. McNaught and A. Wilkinson, Blackwell Scientific Publications, Oxford (1997). XML on-line corrected version: http://goldbook.iupac.org (2006-) created by M. Nic, J. Jirat, B. Kosata; updates compiled by A. Jenkins, doi:10.1351/goldbook.L03540.
Declaration (37 CFR 1.63) for Utility Patent Application and Assignment of Rights, Title and Interest in Invention of Edward L. Sughrue II, filed in U.S. Appl. No. 14/230,835, filed Dec. 16, 2015, Exhibit 2014 in Inter Partes Review No. IPR2018-01374.
Declaration of Dr. Michael T. Klein, dated Jun. 3, 2019, Exhibit 2029 in Inter Partes Review No. IPR2018-01374.
Declaration of Jukka Pekka Myllyoja, dated Jun. 3, 2019, Exhibit 2024 in Inter Partes Review No. IPR2018-01374.
Declaration of Petri Yngve Lindqvist, dated Jun. 3, 2019, Exhibit 2019 in Inter Partes Review No. IPR2018-01374.
Office Action issued in U.S. Appl. No. 11/415,707 dated Aug. 24, 2007.
Patent Owner Response, dated Jun. 3, 2019 in Inter Partes Review No. IPR2018-01374.
Periodic Table of the Elements downloaded at https://sciencenotes.org/printable-periodic-table/ on Nov. 19, 2018, Exhibit 2002 in Inter Partes Review No. IPR2018-01374.
Petition, Paper #2 in Inter Partes Review No. IPR2018-01374, May 2019.
Prehydrogenation, Hydrodeoxygenation and Countercurrent Isomerization of Rapeseed Oil (undated).
Certified English Translation of "The Identification of Wear Metals in Used Lubricants with the Help of a Plasma Emission Spectrometry," Neste Corporation Technology Work Instruction EO 043, Rev 6 (Dec. 29, 1997), Exhibit 2032 in Inter Partes Review No. IPR2018-01374.
TOFA Laboratory Report, Summit Environmental Technologies, issued Feb. 27, 2013 (Ex. 1004 in IPR2013-00178).
European Committee for Standardization (CEN), EN 12441-4, Zinc and zinc alloys—Chemical analysis, Part 4: Determination of iron in zinc alloys—Spectrophotometric method, 2003 (DIN, Berlin, Germany).
Abhari et al., "New Routes to Ethylene," EEPC Seminar in Berlin, Germany (2010).
Adarme, R. et al., "Demetallization of Asphaltenes: Thermal and Catalytic Effects with Small-Pore Catalysts," Abstracts of Papers Part 2, American Chemical Society 200th National Meeting (Aug. 1990), Exhibit 2005 in Inter Partes Review No. IPR2018-01374.
Antoniassi, R. et al., "Pretreatment of Corn Oil for Physical Refining," JAOCS, vol. 75, No. 10, 1998, pp. 1411-1415.
Bartholomew, Calvin H., "Mechanisms of Catalyst Deactivation," Applied Catalysis A: General, 212 (2001): 17-60 (Ex. 2006 in IPR2014-00192 for U.S. Pat. No. 8,278,492).
Bauldauf et al., "Processing of Vegetable Oil to Fuels in Mineral Oil Refinery Processes," VOE Reports, No. 1126 (1994) pp. 153-168.
Beare-Rogers, J., et al., "Lexicon of Lipid Nutrition" (IUPAC Technical Report), Pure Appl. Chem., vol. 73, No. 4, pp. 685-744, 2001.
Bergerioux, C. et al., "Determination of Trace Element Pathways in a Petroleum Distillation Unit by Instrumental Neutron Activation Analysis," Journal of Radioanalytical Chemistry, vol. 54, No. 1-2, 1979, pp. 255-265.
Carman, P.C., "Fluid Flow Through Granular Beds," Trans IChemE, vol. 75, (1997), Exhibit 1029 in Inter Partes Review No. IPR2018-01374.
Cecchi, G. et al., "Conversion des huiles végétales en carburants potentiels, Essais préliminaries," Revue Francaise des Corps Gras, No. 9, 397-401 (1987).
Da Rocha Filho, G. N. et al. "Catalytic Conversion of Hevea Brasiliensis and Virola sebifera Oils to Hydrocarbon Fuels," JAOCS, vol. 69 No. 3, 266-271 (1992).
Deem, A.G. et al., "Catalytic Poisoning in Liquid-Phase Hydrogenation," Industrial and Engineering Chemistry, vol. 33. No. 11, Nov. 1941, pp. 1373-1376.
Edgar, M.D., "Analysis is key to hydrotreater troubleshooting," Oil & Gas Journal, vol. 82, Issue 23, Jun. 4, 1984. pp. 67-70.
Declaration of Edward Sughrue dated Nov. 21, 2013, Exhibit 1002 in *Syntroleum* v. *Neste* IPR2014-00192.
Search Report dated Jun. 1, 2011, by European Patent Office for Application No. 11154437.5.

(56) References Cited

OTHER PUBLICATIONS

Ergun, S., "Fluid Flow Through Packed Columns," Chemical Engineering Progress vol. 48, No. 2, pp. 89-94, Exhibit 1024 in Inter Partes Review No. IPR2018-01374, Feb. 1952.
Evans, et al., "Iron and Phosphorus Contents of Soybean Oil from Normal and Damaged Beans," Journal of the American Oil Chemists' Society, vol. 51. No. 10, pp. 444-448 (1974), Exhibit 1020 in Inter Partes Review No. IPR2018-01374.
Feng, Y. et al., "Chemical composition of tail-oil based cetane enhancer tor diesel fuels," First Biomass Conference of the Americas: Energy, Environment, Agriculture, and Industry, vol. II, Aug. 30-Sep. 2, 1993, Burlington, Vermont, p. 863-875 (1993).
Furimsky, E., "Catalytic Hydrodeoxygenation," Applied Catalysis A: General 199 (2000) 147-190.
Galperin, L. B., "Hydroisomerization of N-decane in the presence of sulfur and nitrogen compounds," Applied Catalysis A: General 209 (2001) 257-268.
Garrido, M.D., et al., "Concentrations of metals in vegetable edible oils," Food Chemistry, vol. 50 (1994) pp. 237-243.
Declaration of James G. Goodwin, Jr., Ph.D. under 37 C.F.R. § 1.132, dated Nov. 13, 2012, cited in Reexamination Control No. 95/002,084.
Gunstone, F., The Lipid Handbook, 2d. Ed. (1994), Exhibit 1009 in Inter Partes Review No. IPR2018-01374.
Gusmao, et al., "Utilization of Vegetable Oils as Alternative Source for Diesel-Type Fuel," Catalysis Today, 5:533-544 (1989).
Huve, L.G., "Shell Global Solutions Dewaxing Technologies & Catalysts Current Status," pp. 1-13, Dec. 14, 2007.
Jongpatiwut, S. et al., "Competitive hydrogenation of poly-aromatic hydrocarbons on sulfur-resista nt bimetallic Pt—Pd catalysts," 262 Applied Catalysis A: General 241-253 (2004), Exhibit 2007 in Inter Partes Review No. IPR2018-01374.
Kubicka et al., "Ultraclean Fuels Obtained by Hydrodeoxygenationof Renewable Feedstocks: Deactivation of Deoxygenation Catalysts," Prep. Pap.-Am. Chem. Soc., Div. Fuel Chem., (2010), vol. 55, No. 1, p. 169-170.
Declaration, Power of Attorney, and Petition of Edward L. Sughrue II, filed in U.S. Appl. No. 12/877,328, filed Sep. 8, 2010, Exhibit 2012 in Inter Partes Review No. IPR2018-01374.
Laurent, E. & Delmon, B., "Study of the Hydrodeoxygenation of Carbonyl, Carboxylic and Guaiacyl Groups over Sulfided CoMo/γ-Al2O3 and NiMo/γ-Al2O3 Catalysts. II. Influence of water, ammonia and hydrogen sulfide," 109 Applied Catalysis, 1994, pp. 97-115 ("Laurent II").
MacDonald, "Fuel From Fats," ener G Alternative Sources Magazine (Sep./Oct. 2011).
Mag, T., "Canola Seed and Oil Processing," Canola Council of Canada, 1994.
Marangozis, J., "Rate and Mechanism of Hydrogenation of Cottonseed Oil in Slurry Reactors," Ind. Eng. Chem., Process Des. Dev., vol. 16, No. 3 (1977).
Miller, S.J., "Studies on Wax Isomerization for Lubes and Fuels, Zeolited and Related Microporous Materials: State of the Art in 1994," Studies in Surface Science and Catalysts, 84:2319-2326 (1994).
Declaration of Nelson E. Lawson (with Tab A) dated Mar. 3, 2013 in Inter Parte Review No. IPR2013-00178.
Nunes, et al., "Soybean Oil Hydrocracking Under Pressure Process and General Aspect of the Transformation," Revue De L'institut Fransais Du Petrole, vol. 42, No. 3, May-Jun. 1986.
Phillips, M.D. et al., "Effect of Silicon on Hydrotreating of Petroleum Residua," 9(3) Fuel Science and Technology Int'l, 305-319 (1991), Exhibit 2004 in Inter Partes Review No. IPR2018-01374.
Prakash, Dr. C. B., "A Critical Review of Biodiesel as a transportation fuel in Canada," GCSI—Global Change Strategies International Inc. (1998).
Przybylski, R., "Canola Oil: Physical and Chemical Properties," Canola Council of Canada; no date provided.
Ribamar et al. "Catalytic Decomposition of Vegetable Oil," Applied Catalysis, vol. 5., 1983, pp. 299-308.
Ribamar et al., "Vegetable Oil Catalytic Breakdown," Petrobras Technical Bulletin, Rio de Janeiro, 24 (2): 139-147, Apr./Jun. 1981.
Rinard, I., "Material Balance Notes" (1999), Exhibit 1028 in Inter Partes Review No. IPR2018-01374.
Santana, R. et al., "Evaluation of different reaction strategies for the improvement of cetane number in diesel fuels," 85 Fuel 643-656 (2006), Exhibit 2009 in Inter Partes Review No. IPR2018-01374.
Satikunaporn, M., et al., "Ring opening of decalin and tetralin on HY and Pt/HY zeolite catalysts," 228 Journal of Catalysis, pp. 100-113 (2004), Exhibit 2008 in Inter Partes Review No. IPR2018-01374.
Soveran, D.W. et al., "The Effect on Diesel Engine Emissions with High Cetane Additives from Biomass Oils," (1992).
Spataru, "Is There a Future for Yellow Grease as a Fuel Additive?," Render 12-14 (Feb. 2001).
Stumborg, M., et al., "Hydroprocessed Vegetable Oils for Diesel Fuel Improvement," Liquid Fuels, Lubricants and Additives from Biomass, Proceedings of an Alternative Energy Conference (1994).
Sughrue, E.L. et al., "Kinetics of Carbon Monoxide Methanation on Nickel Monolithic Catalysts2," Applied Catalysis, 239-256 (1982), Exhibit 2006 in Inter Partes Review No. IPR2018-01374.
Deposition Transcript of Edward Lawrence Sughrue II, May 21, 2019, Exhibit 2031 in Inter Partes Review No. IPR2018-01374.
Declaration of Edward L. Sughrue II dated Mar. 7, 2013 in Inter Parte Review No. IPR2013-00178.
Declaration of Edward L. Sughrue II dated Aug. 1, 2018, Exhibit 1002 in Inter Partes Review No. IPR2018-01374.
Swartz, M. Method Validation, in Handbookof Methods and Instrumentation in Separation Science, vol. 1, 614-620 (Colin Poole ed., 2009), Waters Corporation, Milford, MA, USA.
Tyson, K. et al., "Biomass Oil Analysis: Research Needs and Recommendations," Technical Report, National Renewable Energy Laboratory, Colorado (2004).
Viljava, T., "From Biomass to Fuels: Hydrotreating of Oxygen-Containing Feeds on a CoMo/Al2O3 Hydrodesulfurization Catalyst" (2001).
Wong, A. et al., "Conversion of Vegetable Oils and Animal Fats into Paraffinic Cetane Enhancers for Diesel Fuels," Second Biomass Conference of the Americas (1995).

\* cited by examiner

USE OF RENEWABLE OIL IN HYDROTREATMENT PROCESS

CROSS-REFERENCE TO RELATED APPLICATIONS

This application claims the benefit of priority of U.S. patent application Ser. No. 14/932,566, filed Nov. 4, 2015, now U.S. Pat. No. 9,969,940 issued May 15, 2018 in turn, to U.S. patent application Ser. No. 14/273,024, filed May 8, 2014, now U.S. Pat. No. 9,206,092 issued Dec. 8, 2015, in turn, to U.S. patent application Ser. No. 13/397,236, filed Feb. 15, 2012, now. U.S. Pat. No. 8,742,185 issued Jun. 3, 2014, in turn, to U.S. Provisional Application No. 61/443,161 filed Feb. 15, 2011, the entire contents of which are herein incorporated by reference. U.S. patent application Ser. No. 13/397,236 also claims the benefit of priority under 35 U.S.C. § 119 to European Patent Application No. 11154437.5 filed in Europe on Feb. 15, 2011, the entire contents of which are herein incorporated by reference.

FIELD

Disclosed is the use of renewable oil in a hydrotreatment process, for example, for the production of hydrocarbons. Also disclosed is the use of renewable oil comprising less than 1 ppm of iron, for the production of liquid fuel components or components which can be converted to liquid fuels.

BACKGROUND INFORMATION

Liquid fuel components are mainly based on crude oil. There is an ever growing demand for liquid fuels with lower $CO_2$ emissions compared to crude oil based fuels. Various renewable sources have been used as alternatives for crude oil fuels. Methods for converting biomass to liquid fuels include transesterifications of triglycerides to alkylester, hydrotreatment of oils and fats to paraffins, and renewable diesel obtained through gasification and the Fischer-Tropsh process. One of the most promising and furthest developed method is hydrogenation of vegetable oil (HVO) or animal fats to produce paraffins, which can further be refined, e.g., through isomerisation reactions to renewable diesel with excellent properties.

Vegetable oils and animal based fats can be processed to decompose the ester and/or fatty acid structure and to saturate the double bonds of the hydrocarbon backbone thus obtaining about 80-85% of n-paraffins relative to the mass of the starting material. This product can be directly used as a middle distillate fuel component. The cold flow properties of n-paraffins can be enhanced in an isomerisation step where iso-paraffins are formed. A method of producing iso-paraffins from vegetable oils and animal fats is presented in European Patent Document No. EP 1 396 531.

Certain impurities present in the renewable oil can be harmful for the performance of the hydrotreatment/deoxygenation catalyst. Triglycerides can be converted to hydrocarbons through a hydrodeoxygenation pathway using classical hydrodesulphurisation (HOS) catalyst such as NiMo and CoMo HOS catalysts. However, the catalyst has been shown to be deactivated as a result of phosphorous in the feedstock. In publication Kubicka et al (2010) it is shown that elimination of phosphorous from the feedstock is crucial to prevent rapid catalyst deactivation.

U.S. Patent Application Publication No. 2007/0010682 discloses a process for the production of diesel range hydrocarbons from bio oils and fats, which method includes hydrodeoxygenation and hydroisomerisation to achieve fuel components with excellent performance. It is also acknowledged that in order to avoid catalyst deactivation and undesired side reactions the amount of alkali metals and alkaline earth metals are less than 1 w-ppm calculated as elemental metal and phosphorus content less than 5 w-ppm. Degumming and bleaching are suggested to remove the impurities from the feed. In bleaching the refined oil feed is heated and mixed with natural or activated bleaching clay to remove impurities such as chlorophyll, phosphoric compounds and metals remaining in the oil after degumming.

There exist numerous commercial bleaching clays, which can be used in the bleaching of renewable oils. European Patent Document No. EP 0 507 217 discloses a porous base-treated inorganic adsorbent for removal of contaminants such as free fatty acids and metals from glyceride oils. The adsorbent is capable of reducing the levels of phosphorus to below 0.3 ppm and the level of metals to below 0.1 ppm.

In previous laboratory scale experiments it has been shown that triglycerides, e.g., in vegetable oils can be converted to hydrocarbons in hydrotreatment reactions. However, in large scale production of hydrotreated vegetable oil some difficulties have occurred over time. A significant increase in the pressure drop over the hydrodeoxygenation catalyst bed was observed. In normal running conditions there is a higher pressure at the top of the catalyst bed compared to the pressure at the bottom of the catalyst bed and this difference is called the pressure drop. The pressure drop drives the feed stream forward in the reactor. Over time, continuous plugging of the catalyst increases the pressure drop and could lead to complete plugging of the flow in the catalyst bed. An increase in the pressure drop was observed after some production time even if the feed contained only trace amounts of phosphorous and metal impurities such as Na, Ca and Mg.

These findings indicate that the hydrotreatment of glyceride oils from renewable sources still needs improvements and especially large scale production encounters problems which could not have been foreseen from the early laboratory scale experiments.

SUMMARY

According to an exemplary aspect, disclosed is a method for preparing a hydrocarbon, the method comprising: subjecting a bio oil from at least one renewable source to a hydrotreatment process, wherein in the hydrotreatment process, hydrocarbons are formed from said bio oil in a catalytic reaction employing a catalyst, wherein an iron content of said bio oil is less than 1 w-ppm calculated as elemental iron.

DETAILED DESCRIPTION

Figure 1:
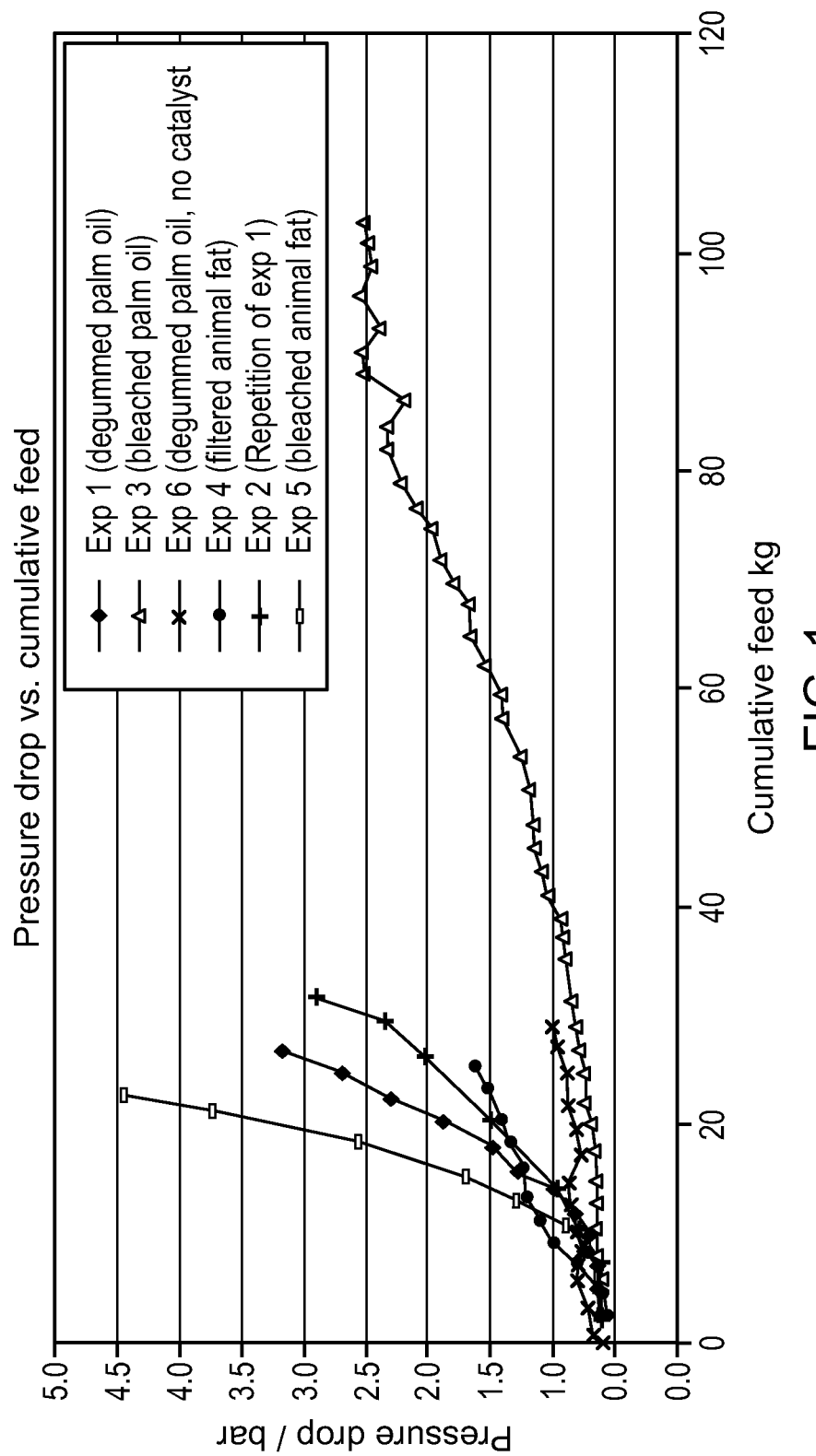
FIG. 1 shows the pressure drop over the catalyst bed in relation to the cumulative feed, in accordance with an exemplary aspect.

Disclosed is the use of bio oil from at least one renewable source, in a hydrotreatment process, in which process hydrocarbons are formed in a catalytic reaction and the iron content of the bio oil is less than 1 w-ppm, for example, less than 0.5 and, for example, less than 0.25 w-ppm calculated as elemental iron. The use of bio oil with extremely low content of iron can be employed to reduce or avoid plugging of the catalyst used in the hydrotreatment reaction.

An exemplary embodiment relates to the use of a glyceride oil from at least one renewable source in a hydrotreatment process, in which process hydrocarbons are formed in a catalytic reaction and the iron content of the glyceride oil is less than 1 w-ppm, for example, less than 0.5 w-ppm and, for example, 0.25 w-ppm calculated as elemental iron.

The hydrotreating catalyst was found to be plugged, for example, in large scale production over a certain time. The particles responsible for the plugging of the catalyst were found upon analysis to contain high amounts of phosphorous and metals. Further studies lead to the surprising finding that the iron content of the feed used in the hydrotreatment process is responsible for the plugging of the catalyst. An exemplary aspect therefore relates to renewable oil with very low iron content as the starting material for a hydrotreatment process.

Renewable oil enables longer running time of hydrotreating catalysts without plugging. Previous studies have established that impurities such as phosphorous and Na, Ca and Mg metals present in the feedstock may be responsible for deactivation of the catalyst. An exemplary aspect can address the problem of catalyst plugging and ensure smooth running of the process and stable reaction conditions allowing manufacture of hydrocarbons from glyceride oil with high conversion rate and high selectivity.

In addition, an exemplary aspect can prevent the hydrotreating catalyst from deactivation, or reduce the degree of deactivation, and the low amount of Fe in the oil minimises the oxidation of the renewable oil. Iron compounds can act as oxidants.

Here, bio oil is understood to mean any oil originating from a renewable (bio) source, including, for example, vegetable, animal or microbial sources. Bio oils can comprise at least fatty acids or fatty acid derivatives such as glycerides, alkyl esters of fatty acids, fatty acid alcohols or soaps.

Here, glyceride oil is understood to mean any oil which comprises triacylglycerides. The glyceride oil may also comprise di- and monoacylglycerides as well as fatty acids and their derivatives such as alkyl esters especially methyl esters. The chain length of the hydrocarbon chains in the glyceride oil can be from at least C8 up to C24. The term glyceride oil is meant to include at least, but not limited to rapeseed oil, colza oil canola oil, tall oil, sunflower oil, soybean oil, hempseed oil, cottonseed oil, corn oil, olive oil, linseed oil, mustard oil, palm oil, peanut oil, castor oil, coconut oil, camellia oil, jatropha oil, oils derived from microbial sources, which are possible genetically modified and includes at least algae, bacteria, moulds and filamentous fungi; animal fats, fish oil, lard, tallow, train oil, recycled fats from the food industry and any mixture of the oils.

Here, oil from renewable source or renewable oil is understood to mean any oil originating from a source that can be considered renewable, i.e., not fossil. Renewable sources include at least all plant (vegetable) and animal based sources, but also microbial based sources such as algae, bacteria, moulds and filamentous fungi etc. Re-use of spent oil from food industry is also considered a renewable source as well as oils obtained by conversion of wastes, such as municipal and slaughterhouse wastes.

Here the term hydrotreatment includes at least hydrodeoxygenation (HDO) and is understood as a collective term for all catalytic processes, which removes oxygen from organic oxygen compounds in the form of water, sulphur from organic sulphur compounds in the form of dihydrogen sulphide ($H_2S$), nitrogen from organic nitrogen compounds in the form of ammonia ($NH_3$) (hydrodenitrogenation, HDN) and halogens, for example chlorine from organic chloride compounds in the form of hydrochloric acid (HCl) (hydrodechlorination, HDCl), for example, under the influence of sulphided NiMo or sulphided CoMo catalysts. Hydrotreatment is here understood to include also decarboxylation/decarbonylation, i.e., removal of oxygen in the form of $CO_X$.

Hydroisomerisation or isomerisation is here understood to mean any process in which branches on the hydrocarbon backbone are formed and isoparaffins are produced. For example, methyl and ethyl side-chains are formed in the isomerisation step.

Disclosed is the use of bio oil, for example, glyceride oil, from at least one renewable source in a hydrotreatment process, in which process hydrocarbons are converted from the bio oil in a catalytic reaction and the iron content of the bio oil is less than 1 w-ppm, for example, less than 0.5 w-ppm, and, for example, less than 0.25 w-ppm, calculated as elemental iron. The hydrotreatment process is any catalytic process, such as a hydrodeoxygenation process performed using a trickle-bed reactor, in which, for example, glyceride oil material is treated with hydrogen to form hydrocarbons. Hydrodeoxygenation can be performed under a pressure from 10 to 150 bar, at a temperature of from 200 to 400° C. and using a hydrogenation catalyst containing metals from Group VIII and/or VIB of the Periodic System. For example, the hydrogenation catalysts are supported Pd, Pt, Ni, NiMo or CoMo catalyst, the support being alumina and/or silica. Exemplary catalysts are NiMo/Al2O3 and CoMo/Al2O3.

In order to improve the properties, especially the cold flow properties, of the formed hydrocarbons, the hydrotreatment step can be followed by an isomerisation step. In the isomerisation step the hydrocarbons undergo an isomerisation reaction whereby isoparaffins are formed.

A rapid increase in the pressure drop of the hydrotreatment reactor was noticed to occur in large scale production facilities. The reactor was opened and a substantial amount of dust-like particles was found inside the reactor. The dust-like particles were believed to be the cause of the plugging and increase in pressure drop over the catalyst bed. Analyses of dust-like particles revealed metals originating from feedstock (mainly Fe, Ca, Mg, Na) as well as phosphorus and carbon. Introducing less contaminated feedstock into the process has dramatically decreased the rate of pressure drop increase in the hydrotreating reactor. The plugging phenomenon was studied in more detail with a set of laboratory reactor experiments illustrated in the examples.

Based on the experiments with palm oil having very low level of impurities, a catalyst cycle length based on catalyst deactivation with pure feedstock can be calculated. Furthermore, based on plant operating experience the rate of reactor plugging can be correlated with iron content. From this information, it can be concluded that bio-based feedstock (glyceride oil) to be used as feed material for hydrotreatment reaction can be purified to iron content of less than 1 to 0.2 w-ppm (depending on the dimensioning design WHSV of the hydrodeoxygenation reactor and expected life cycle of the catalyst), for example, in order not to shorten the catalyst cycle length due to pressure drop increase. For efficient and profitable plant operation, the Fe content of the feedstock of the hydrogenation reactor can be less than 0.5 w-ppm, for example, less than 0.25 w-ppm (w-ppm refers here to ppm by weight). This purification result can be obtained (depending on used feedstock) using pre-treatment methods, such as degumming and bleaching, or alternatively new pre-treatment technologies or a combination thereof. Thus, disclosed is a glyceride oil intermediate, which intermediate consists of glyceride oil from at least one renewable source and the iron content of said glyceride oil is less than 1 w-ppm calculated as elemental iron, for example, less than 0.5 w-ppm and, for example, less than 0.25 w-ppm.

EXAMPLES

Undiluted glyceride oil was fed with high WHSV (8-10) through a bed consisting of hydrotreatment catalyst diluted in 1:2 ratio with quartz sand. Sand dilution was estimated to act as a filter, magnifying the plugging effect of the dust-like particles. This setup enabled reactor plugging to occur in days rather than months as in a reactor on an industrial scale plant. The reactor was considered to be plugged when a pressure drop of 3 bar was reached across the reactor, initial pressure being bar.

First, a reference run (plant reference run) was conducted with degummed palm oil as the glyceride oil feed having rather high level of impurities (Experiment 1). Experiment 1 was repeated (Experiment 2). This test was repeated without any catalyst to demonstrate the effect of presence of catalyst in reactor plugging (Experiment 6). Experiments were then continued with bleached palm oil having very low levels of impurities (Experiment 3), filtered animal fat with high levels of P and Na but almost no other metals (Experiment 4), and finally bleached animal fat with moderate levels of P and Fe but almost no other metals (Experiment 5).

A summary of the conducted experiments is shown below:
Plant reference run with degummed palm oil (Experiment 1)
Repetition of experiment 1 with degummed palm oil (Experiment 2)
A run with bleached palm oil (Experiment 3)
A run with filtered animal fat (Experiment 4)
A run with bleached animal fat (Experiment 5)
A run with degummed palm oil repeated without catalyst (Experiment 6)

The composition of the dust-like particles was determined and the amount of the dust-like particles was measured after the experiment by separating the quartz sand and dust-like particles from the catalyst by screening and analysing the sand+dust mixture with wave length dispersive a X-ray fluorescence spectrometer (Bruker AXS S4 Explorer), with helium as measurement atmosphere.

The results of the analyses in the experiments are shown in following Table 1.

TABLE 1

Total increase in pressure drop, total cumulative feed through reactor; feed impurity levels, impurities found in catalyst, impurities found in sand + dust

| | Experiment No. | | | | | |
|---|---|---|---|---|---|---|
| | 1 | 2 | 3 | 4 | 5 | 6 |
| Initial dP/bar | 0.55 | 0.62 | 0.62 | 0.62 | 0.61 | 0.59 |
| Final dP/bar | 3.8 | 2.9 | 2.5 | 1.6 | 4.44 | 1.0 |
| delta(dP)/bar | 3.25 | 2.28 | 1.88 | 0.98 | 3.83 | 0.41 |
| Cumulative feed kg | 31.8 | 31.6 | 10.27 | 25.3 | 22.6 | 28.9 |
| Plugging rate mbar/kgfeed | 102.1 | 72.1 | 18.3 | 38.8 | 169.7 | 14.2 |
| Feed impurity concentrations | | | | | | |
| P/ppm | 3.8 | 3.7 | 0.6 | 24 | 5.7 | 3.8 |
| Ca/ppm | 1.2 | 1.1 | 0.3 | 0.6 | 0.1 | 1.2 |
| Fe/ppm | 1.2 | 1.3 | 0.6 | 0.1 | 1.8 | 1.2 |
| Na/ppm | 1 | 0 | 0 | 6 | 0 | 1 |
| Mg/ppm | 0.2 | 0 | 0 | 0.3 | 0.2 | 0.2 |
| Impurities found in sand + dust | | | | | | |
| P/mg | 425 | 309 | 154 | 154 | 309 | 301 |
| Ca/mg | 77 | 77 | 4 | 4 | 0 | 6 |
| Fe/mg | 116 | 116 | 77 | 54 | 174 | 18 |
| Na/mg | 77 | 39 | 0 | 54 | 0 | 6 |
| Mg/mg | 0 | 0 | 0 | 4 | 0 | 0 |
| Impurities found in catalyst | | | | | | |
| P/mg | 60 | 50 | 20 | 206 | 30 | |
| Ca/mg | 10 | 7 | 5 | 1 | 0 | |
| Fe/mg | 30 | 22.5 | 85 | 14 | 70 | |
| Na/mg | 10 | 12 | 5 | 13 | 0 | |
| Mg/mg | 0 | 0 | 0 | 0 | 0 | |

The pressure drop correlated with cumulative feed in each Experiment is presented in FIG. 1.

Figure 2:
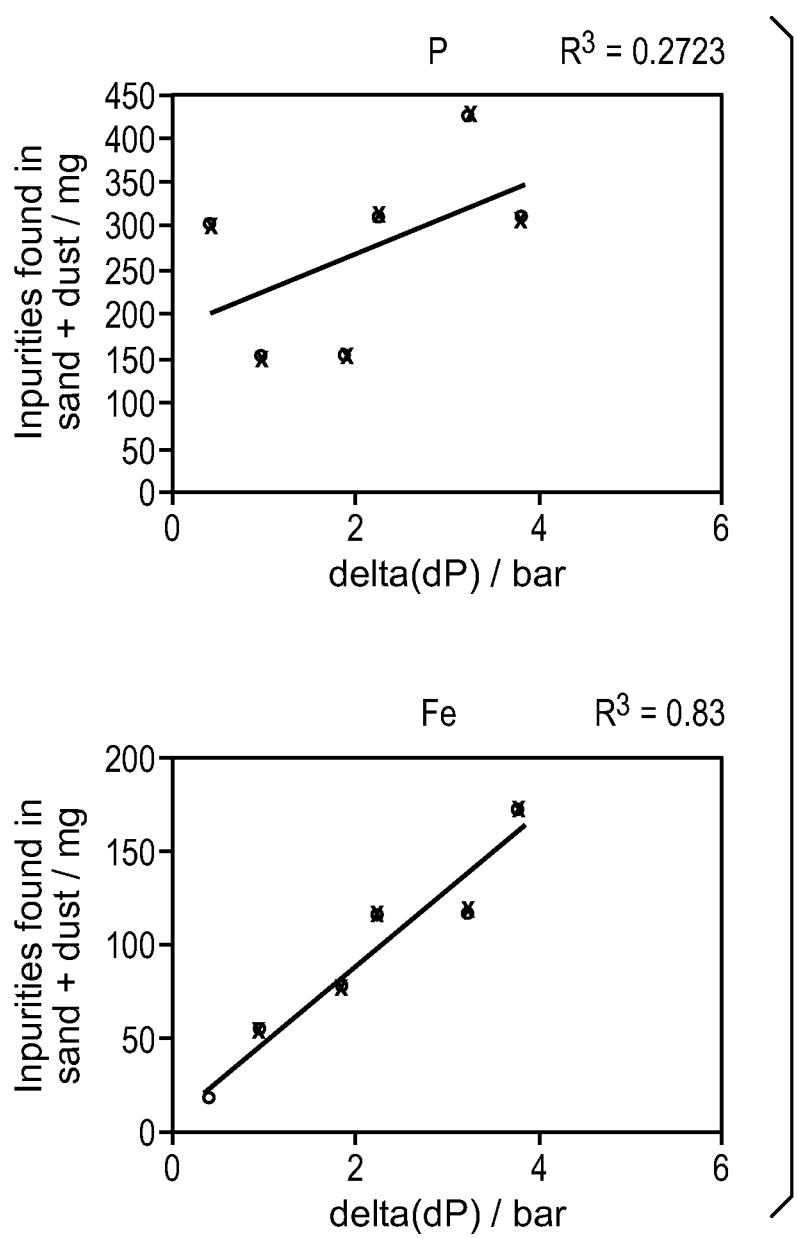
FIG. 2 shows the correlation between absolute increase in pressure drop and absolute masses of P and Fe found in the dust, in accordance with an exemplary aspect.

The absolute amounts of individual impurities in the dust-like particles were then correlated with the absolute pressure drop increases in corresponding experiment. Results are shown as correlation plots with R2-values for P and Fe in FIG. 2 and for all measured impurities in Table 2 below.

TABLE 2

Correlation between absolute increase in pressure drop and absolute masses of impurities found in dust

| Impurity | $R^2$ |
|---|---|
| P | 0.27 |
| Ca | 0.12 |
| Fe | 0.93 |
| Na | 0.01 |
| Mg | 0.18 |

Figure 3:
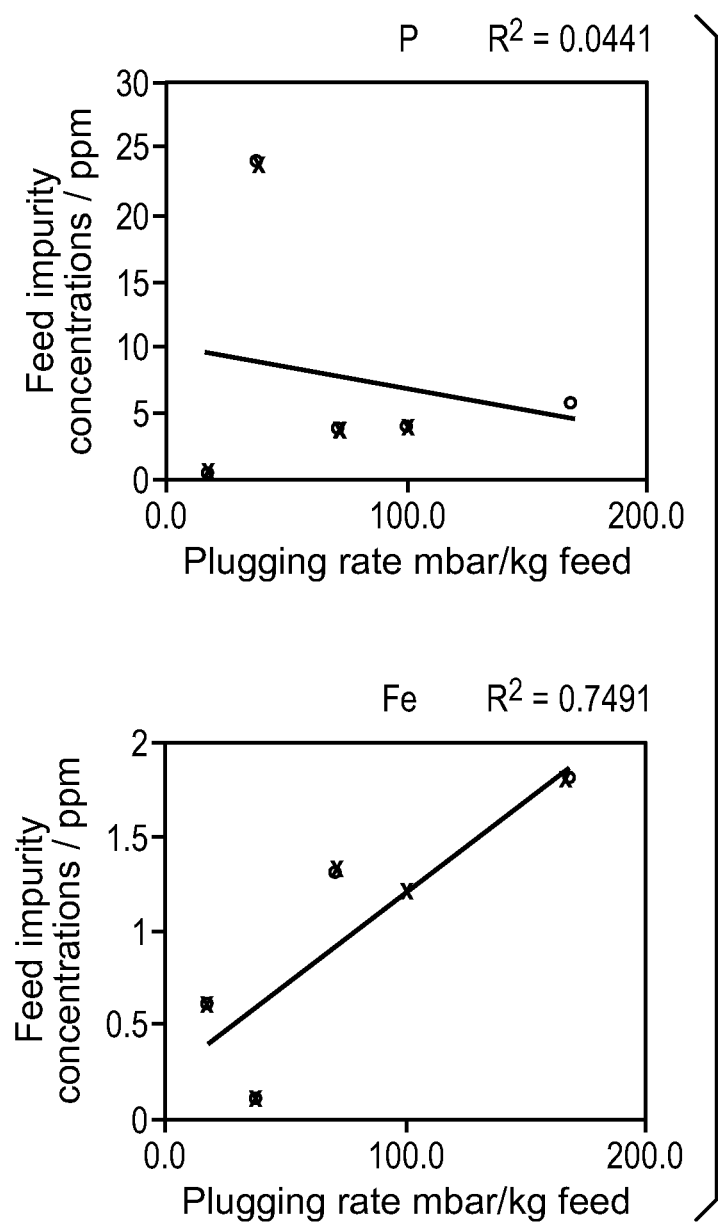
FIG. 3 shows the correlation between rate of increase in pressure drop (in bar/kg (feed) and concentrations of P and Fe in the feed, in accordance with an exemplary aspect.

A relative plugging rate can be calculated for each experiment by dividing the increase in pressure drop with total cumulative feed introduced in the reactor throughout the experiment. Correlating this plugging rate with impurities in corresponding feedstocks gives the plots shown in FIG. 3 for P and Fe. This correlation for all measured impurities is shown in table 3. The experiment without catalyst is excluded from FIG. 3, due to different rate of dust formation with and without catalyst.

TABLE 3

Correlation between rate of increase in pressure drop (in bar/kg(feed) and concentrations of impurities in feed.

| Impurity | $R^2$ |
|---|---|
| P | 0.04 |
| Ca | 0.02 |
| Fe | 0.75 |
| Na | 0.14 |
| Mg | 0.10 |

According to these results, iron is the only impurity in the dust correlating strongly with the increase in pressure drop over the catalyst bed.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A bio oil intermediate for a hydrotreatment process to form hydrocarbons, the bio oil intermediate comprising:
   a bio oil from at least one renewable source, wherein an iron content of said bio oil contains:
   an iron concentration of less than 1 to 0.2 w-ppm calculated as elemental iron;
   a phosphorous concentration of less than 5 w-ppm; and
   a cumulative alkali metals concentration and alkaline earth metals concentration calculated as elemental metal of less than 1 w-ppm.

2. A bio oil intermediate according to claim 1, wherein said bio oil intermediate is a group of bio oils characterized by a result-effective range of iron concentrations to address plugging in a hydrodeoxygenation reactor, the range having a lower bound of 0.2 w-ppm and an upper bound of 1 w-ppm.

3. A bio oil intermediate according to claim 1, in combination with a catalyst bed of a hydrodeoxygenation reactor, wherein the catalyst bed comprises:
   a NiMo catalyst.

4. A bio oil intermediate according to claim 1, in combination with a catalyst bed of a hydrodeoxygenation reactor, wherein the catalyst bed comprises:
   a CoMo catalyst.

5. A bio oil intermediate according to claim 1, in combination with a catalyst bed of a hydrodeoxygenation reactor, wherein the catalyst bed comprises:
   a NiMo/$Al_2O_3$ catalyst.

6. A bio oil intermediate according to claim 1, in combination with a catalyst bed of a hydrodeoxygenation reactor, wherein the catalyst bed comprises:
   a catalyst containing at least one or more of Pd, Pt, Ni, NiMo and CoMo.

7. A bio oil intermediate according to claim 1, in combination with a catalyst bed of a hydrodeoxygenation reactor, wherein the catalyst bed comprises:
   a catalyst containing metals from Group VIII or VIB of the Periodic Table.

* * * * *